United States Patent [19]
Goto et al.

[11] Patent Number: 4,966,973
[45] Date of Patent: Oct. 30, 1990

[54] 2-SUBSTITUTED COUMARAN DERIVATIVES

[75] Inventors: Giichi Goto; Shigenori Ohkawa, both of Osaka; Naohisa Fukuda, Hyogo, all of Japan

[73] Assignee: Takeda Chemical Industries, Ltd., Osaka, Japan

[21] Appl. No.: 363,787

[22] Filed: Jun. 9, 1989

[30] Foreign Application Priority Data

Jun. 10, 1988 [JP] Japan .................. 63-143860

[51] Int. Cl.[5] ........................................ C07D 307/79
[52] U.S. Cl. ................... 546/269; 540/596;
544/298; 546/137; 546/153; 546/191; 546/196;
546/256; 549/462; 549/458; 549/467; 549/470;
548/182; 548/336; 548/454; 548/525
[58] Field of Search ............ 549/462, 458, 467, 470;
540/596; 544/298; 546/137, 153, 191, 196, 256,
269; 548/182, 336, 454, 525

[56] References Cited

U.S. PATENT DOCUMENTS 4,857,516  8/1989  Terao et al. .................... 549/462

FOREIGN PATENT DOCUMENTS 63-88173  4/1988  Japan .

OTHER PUBLICATIONS

CPI Abstract 4854619 WPI Acc. No. 88-145145/21, Abstract of JP-A-88173/1988.
Burton, Graham W., et al., "Antioxidant Activity of Phenols Related to Vitamin E. Are There Chain-Breaking Antioxidants Better than α-Tocopherol?", J. Am. Chem. Soc., vol. 105, pp. 5950-5951 (1983).
Burton, Graham W. et al., "Autoxidation of Biological Molecules. 4. Maximizing the Antioxidant Activity of Phenols", J. Am. Chem. Soc., vol. 107, pp. 7053-7065 (1985).
Okamoto, Kayoko et al., "Synthesis of Quinones having Carboxy- and Hydroxy-Alkyl Side Chains, and their Effects on Rat-Liver Lysosomal Membrane", Chem. Pharm. Bull., vol. 30, No. 8, pp. 2797-2819 (1982).
Yutaka Maruyama et al., "5-Lipoxygenase Inhibitors for the Treatment of Inflammation and Allergy", Chemical Abstracts, vol. 108, Mar. 7, 1988, p. 445, Abstract No. 82107a.
Katsuji Ejiri et al., "Dihydrobenzofuran Derivatives as Antioxidants and Drug Intermediates", Chemical Abstracts, vol. 100, No. 9, Feb. 27, 1989, p. 630, Abstract No. 75294x.

Primary Examiner—John M. Ford
Assistant Examiner—Bernard I. Dentz
Attorney, Agent, or Firm—Wegner & Bretschneider

[57] ABSTRACT

The present invention relates to a compound of the formula

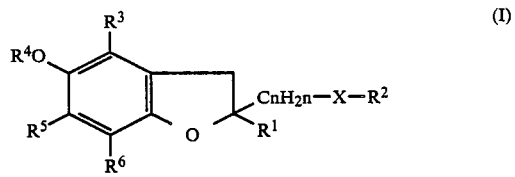

wherein $R^1$ stands for hydrogen or a lower alkyl; n denotes an integer of 1 to 6; X stands for an optionally oxidized sulphur atom, oxygen atom or an optionally substituted imino; $R^2$ stands for methyl or an organic residual group bonded through methylene, methine a quaternary carbon; $R^3$ stands for a lower alkyl; $R^4$ stands for hydrogen or acyl; $R^5$ and $R^6$ each stand for a lower alkoxy or a lower alkyl, or $R^5$ and $R^6$ combinedly stand for butadienylene, and salts thereof.

The compound (I) of the present invention has a strong 5-lipoxygenase inhibiting action, is of high safety and is useful as, among others, an agent for ameliorating dysfunction of circulatory system, an anti-allergic agent and a pharmaceutical agent for central nervous system.

5 Claims, No Drawings

2-SUBSTITUTED COUMARAN DERIVATIVES

This invention relates to novel 2-substituted coumaran derivatives.

The present inventors synthesized various types of coumaran derivatives and found that they had inhibitory actions on 5-lipoxygenase participating in the biosynthesis of leucotrienes and lipoxins, and they have continued the research work diligently to accomplish the present invention.

This invention is to provide a compound represented by the formula:

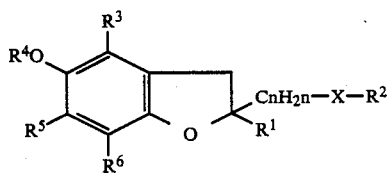
(I)

wherein $R^1$ stand for hydrogen or a lower alkyl; n denotes an integer of 1 to 6; X stands for an optionally oxidized sulphur atom, oxygen atom or an optionally substituted imino; $R^2$ stands for methyl or an organic residual group bonded through methylene, methine or a quaternary carbon; $R^3$ stands for a lower alkyl; $R^4$ stands for hydrogen or acyl; $R^5$ and $R^6$ each stand for a lower alkoxy or a lower alkyl, or $R^5$ and $R^6$ combinedly stand for butadienylene, and salts thereof.

Referring to the compounds represented by the formula (I), the lower alkyl shown by $R^1$ is exemplified by $C_{1-6}$ alkyl such as methyl, ethyl, propyl, i-propyl, butyl, i-butyl, sec-butyl, t-butyl, amyl, hexyl, etc., and especially preferable ones are $C_{1-3}$ alkyl (methyl, ethyl, propyl, i-propyl, etc.).

As the groups shown by $C_nH_{2n}$, mention is made of methylene or straight-chain or branched alkylene.

As the optionally oxidized sulfur atom shown by X, mention is made of sulfide, sulfoxide and sulfone. As the substituents of the imino group, mention is made of aryl such as phenyl, naphthyl, etc. and lower ($C_{1-3}$) alkyl such as methyl, ethyl, propyl, i-propyl, etc.

Examples of methyl and organic residual groups bonded through methylene, methine or quaternary carbon represented by $R^2$ include straight-chain or branched $C_{1-10}$ chain aliphatic hydrocarbon groups such as alkyl, alkenyl, alkynyl, etc., $C_{3-7}$ cyclic hydrocarbon groups (e.g. cyclopropyl, cyclobutyl, cyclopentyl, cyclopentynyl, cyclohexyl, cyclohexenyl, cyclohexadienyl, cycloheptynyl, etc.), aryl (e.g. phenyl, naphthyl, etc.), aryl-$C_{1-3}$ alkyl (e.g. $C_{1-3}$ alkylphenyl, $C_{1-3}$ alkylnaphthyl, etc., such as benzyl, phenethyl, phenylpropyl, α- or β-naphthylmethyl, etc.), and non-aromatic or aromatic 5- to 7-membered monocyclic or condensed poly-cyclic heterocyclic groups (e.g. thienyl, pyridyl, imidazolyl, thiazolyl, pyrrolyl, piperidyl, hexamethylenimidyl, quinolyl, quinuclidyl, indolyl, pyrimidyl, etc.). The above-mentioned methyl or organic residual groups may have a substituent exemplified by hydroxyl group, carboxyl, $C_{1-3}$ alkoxycarbonyl, amino, nitro, cyano, halogen (e.g. fluorine, chlorine, bromine, iodine), $C_{1-3}$ alkoxy, $C_{1-3}$ alkyl, aryl (e.g. phenyl, naphthyl, etc., and these groups may have any of the above-mentioned substituents), $C_{3-6}$ cycloalkyl, heterocyclic groups (e.g. those as mentioned above), etc. When the above-mentioned organic residual groups are alkenyl, they have usually 1 to 5 double bonds optionally conjugated. When they are alkynyl, they have 1 to 5 triple bonds.

Examples of the lower alkyl represented by $R^3$ include $C_{1-6}$ alkyl such as methyl, ethyl, propyl, i-propyl, butyl, i-butyl, sec-butyl, amyl, hexyl, etc., especially $C_{1-3}$ alkyl (methyl, ethyl, propyl, i-propyl, etc.) being preferable.

As the acyl represented by $R^4$, mention is made of carboxylic acid acyl, sulfonic acid acyl, phosphoric acid acyl, etc., preferably those having $C_{1-6}$ substituents (methyl, ethyl, propyl, phenyl, etc.). Especially preferable ones include chain-form ($C_{1-10}$) or cyclic ($C_{3-10}$) alkanoyl, such as formyl, acetyl, propionyl, isobutylyl, decanoyl, cyclopentoyl or benzoyl, optionally quaternized nicotinoyl, succinic acid half-acyl, etc.

Examples of lower alkyls represented by $R^5$ and $R^6$ include $C_{1-6}$ alkyl such as methyl, ethyl, propyl, i-propyl, butyl, i-butyl, sec-butyl, t-butyl, amyl, hexyl, etc., especially $C_{1-3}$ alkyl (methyl, ethyl, propyl, i-propyl, etc.) being preferable. These lower alkyl groups may have a substituent exemplified by hydroxyl group, halogen (fluorine, bromine, chlorine, iodine, etc.), nitro, trifluoromethyl, carboxyl, $C_{1-3}$ alkoxycarbonyl (methoxycarbonyl, ethoxycarbonyl, etc.), 3-pyridyl, 1-imidazolyl, 5-thiazolyl, etc. And, as the lower alkoxy represented by $R^5$ and $R^6$, mention is made of $C_{1-4}$ alkoxy such as methoxy, ethoxy, propoxy, i-propoxy, butoxy, etc.

When $R^5$ and $R^6$, taken together, stand for butadienylene, they form a naphthalene ring, and, as the substituents on the thus-formed benzene ring, mention is made of one to three of lower ($C_{1-3}$) alkyl, lower ($C_{1-3}$) alkoxy (methoxy, ethoxy, propoxy, etc.), hydroxyl group, nitro, halogen, etc.

The compound (I) may, depending on the kinds of substituents thereon, form salts, for example, salts with acids exemplified by organic acids (e.g. acetic acid, propionic acid, oxalic acid, maleic acid, etc.) or inorganic acid (e.g. hydrochloric acid, sulfuric acid, phosphoric acid, etc.), or salts with bases exemplified by alkali metals (potassium, sodium, etc.), alkaline earth metals (calcium, magnesium, etc.), ammonia, etc., especially physiologically acceptable ones being preferable.

A compound (I), when X is a sulfur atom or oxygen atom, can be produced by subjecting a compound represented by the formula:

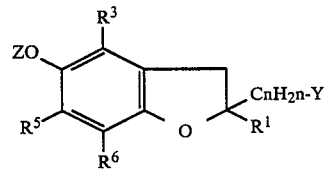
(II)

wherein $R^1$, $R^3$, $R^5$, and $R^6$ are of the same meaning as defined above, Y stands for a leaving group and Z stands for hydrogen or a hydroxyl-protecting group, and a compound represented by the formula:

$$H-X-R^2 \quad (III)$$

wherein X and $R^2$ are of the same meaning as defined above, to substitution reaction, or a compound (I), when X is an imino group, can be produced by subjecting a compound by the formula:

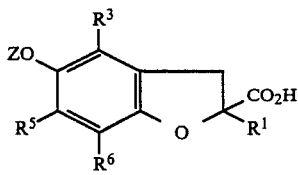

wherein $R^1$, $R^3$, Z, $R^5$ and $R^6$ are of the same meaning defined as above, and a compound (III) to condensation reaction by e.g. an active ester method to produce a corresponding amide compound, followed to reduction by use of e.g. lithium aluminum hydride, then when desired, to deprotection reaction, acylation or/and substituent-exchange reaction.

Examples of the above-mentioned Z include $C_{1-5}$ alkanoyl, and those of Y include halogen, phenyl or an alkyl sulfonic acid residual group.

The substitution reaction is carried out in a solvent such as dimethylformamide, tetrahydrofuran, methanol, ethanol, etc. in the presence of a base such as sodium hydride, potassium carbonate, sodium alcoholate, triethylamine, pyridine, etc. The reaction temperatures usually range from $-20°$ C. to 80° C., and the reaction time ranges from about 0.5 to 24 hours.

While hydrolysis of the acyl group can be carried out under conventional ester-hydrolysis conditions, when the product is basic and unstable to oxygen, the reaction is conducted under argon atmosphere to thereby obtain the desired hydrolyzate in a good yield.

And when the double bond is hydrogenated, the desired compound can be obtained by, employing a catalyst such as palladium-carbon, a conventional method.

The acylation is conducted, by employing a desired acylating agent (e.g. acid anhydride, acid halide), in an organic solvent (e.g. dimethylformamide, acetone, tetrahydrofuran), when necessary, in the presence of a basic catalyst (preferably a base such as sodium hydride, potassium carbonate, pyridine or triethylamine) or an acid catalyst (sulfuric acid, hydrogen chloride, etc.). The reaction temperatures range from about $-10°$ C. to 100° C., and the reaction time ranges from about 10 minutes to 15 hours.

Thus-obtained compound (I) can be isolated by a conventional separation purification means (extraction, chromatography, recrystallization, etc.).

Incidentally, when the compound (I) exists as a diastereomer, it can be isolated into the respective isomers when desired.

And, when the compound (I) is an optionally active one, it can be separated into the d-isomer and l-isomer by a conventional optical resolution means.

The starting compound (II) can be synthesized by, for example, the following method. Namely, a hydroquinone monoacetate (IV) is allowed to react, in the presence of a base, with an aryl halogenide to give an aryl ether (V), and (V) is led to (VI) by Claisen rearrangement. Further, (VI) is processed with bromine in the presence of a base to obtain the compound (II) as a bromomethyl compound.

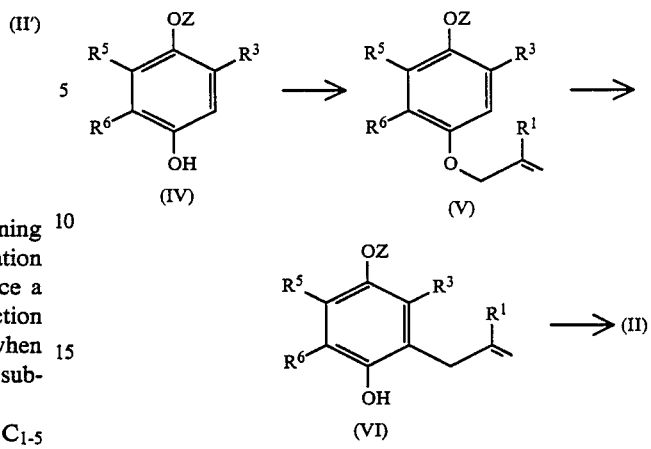

The compound (I) of this invention has an action of inhibiting production of 5-lipoxygenase-type metabolite [leucotrienes, 5-hydroperoxyeicosatetraenoic acid (HPETE), 5-hydroxyeicosatetraenoic acid (HETE), lipoxins, leucotoxins, etc., and therefore, it can be used advantageously as an agent acting on the central nervous system, an agent for ameliorating dyfunction of the circulatory system, an anti-allergic agent, etc.

The compound (I) can be safely administered, orally or non-orally, singly or as a pharmaceutical composition prepared by mixing the compound (I) with a per se known pharmaceutically acceptable carrier, excipient, etc. (e.g. tablet, capsule, liquid, injection, suppository), to mammals (rat, horse, cow, monkey, human, etc.). While the dosage varies with subjects of administration, administration routes, symptoms, etc., in the case of, for example, administering orally to an adult patient suffering from diseases of circulatory system, it is convenient to administer about 0.1 mg/kg to 20 mg/kg/body weight/dose, preferably 0.2 mg/kg to 10 mg/kg/body weight, once to three times a day.

EXPERIMENTAL EXAMPLE 1

5-Lypoxygenase Inhibiting Action

In 0.5 ml of MCM (mast cell medium) was suspended $10^7$ of rat basophilic leukemia (RBL-1) cells. To this suspension was added the test solution previously prepared [consisting of 0.5 ml of MCM, 50 $\mu$m of arachidonic acid, 10 $\mu$g of calcium ionophore A-23187 and the test compound (final concentrations 10 $\mu$M, 1 $\mu$M, 0.1 $\mu$M and 0.01 $\mu$M)], and the reaction was allowed to proceed at 37° C. for 20 minutes. To the reaction mixture was added 4 ml of ethanol, which was shaken sufficiently, followed by leaving the resultant mixture standing for 10 minutes at room temperatures. The resultant mixture was subjected to a centrifuge (2000 rpm) for 10 minutes, then the supernatant was separated. Thus-separated supernatant was concentrated to dryness under reduced pressure. To the concentrate was added 0.5 ml of a 60% aqueous methanol. A 100 $\mu$l portion of this solution was taken and subjected to high performance liquid chromatography to determine 5-HETE (5-hydroxyeicosatetraenoic acid) quantitatively. UV absorption of 5-HETE at 237 nm was measured with a UV absorption monitor. The inhibitory effect (IE) of 5-HETE is expressed by (1-b/a) x 100. In this formula, a means the height of the peak or the area of the peak in the case of presence of no compound (I), while b means the height of the peak or the area of the peak in the case of containing the compound (I). The results revealed, as shown in Table 1, that the test compounds showed strong inhibitory action on the production of 5-HETE.

TABLE 1

| | Effect of Inhibiting 5-Lipoxygenase | | | |
|---|---|---|---|---|
| | % Inhibition (IE) | | | |
| Compound | $10^{-5}$M | $10^{-6}$M | $10^{-7}$M | $10^{-8}$M |
| 1 | 100 | 100 | 64 | 13 |
| 3 | 100 | 100 | 100 | 42 |
| 5 | 100 | 100 | 48 | 24 |
| 7 | 100 | 100 | 45 | — |
| 9 | 100 | 100 | 96 | 8 |
| 11 | 100 | 100 | 19 | — |
| 13 | 100 | 100 | 8 | — |
| 15 | 100 | 100 | 19 | 10 |
| 17 | 100 | 100 | 88 | — |
| 19 | 100 | 99 | 87 | −5 |
| 21 | 100 | 100 | 98 | 18 |
| 25 | 95 | 99 | 94 | 14 |

EXAMPLES

By the following Reference Examples, Examples and Formulation Examples of the compounds of the present invention, the present invention will be described in a more concrete manner, but the present invention is not to be limited thereto.

REFERENCE EXAMPLE 1

To a solution of 4-acetoxy-2,3,5-trimethylphenol [20 g (103 mmol)] and methallyl chloride [10 g (110.4 mmol.)] in dimethylformamide (160 ml) was added potassium carbonate [15.2 g (110 mmol.)]. The mixture was stirred for 3 hours at 80° C. under argon atmosphere. The reaction mixture was, after cooling, diluted with water and then was subjected to extraction with ethyl acetate. The extract was washed with water and dried, then the solvent was distilled off. The residue was crystallized from hexane to obtain the desired 4-acetoxy-2,3,5-trimethylphenyl-2-methylpropenyl ether [18.5 g (yield 72.4%)], m.p.44° to 45° C.

In a manner as above, 4-acetoxy-2,3,5trimethylphenyl allyl ether was synthesized. (Yield 76.7%, m.p. 40° to 41° C.).

REFERENCE EXAMPLE 2

In N,N-diethylaniline (100 ml) was dissolved 4-acetoxy2,3,5-trimethylphenyl 2-methylpropenylether [16.2 g (6.5 mmol)], which was heated at 200° C. for two hours. The reaction mixture was cooled and diluted with isopropyl ether, which was washed with 2N-HCl to remove N,N-diethylaniline. The remainder was washed with a saturated aqueous solution of sodium hydrogencarbonate, which was dried, followed by distilling off the solvent. The residue was crystallized from isopropylether-hexane to obtain the desired 4-acetoxy-2-(2-methyl-2-propenyl)3,4,6-trimethylphenol [14.9 g (yield 91.7%)], m.p. 109 - 110° C.

In a manner similar to the above, 4-acetoxy-2-allyl3,4,6-trimethylphenol was synthesized. (Yield 94.6%, m.p. 117°-118° C.).

REFERENCE EXAMPLE 3

To a chloroform (15 ml) solution of 4-acetoxy-2-allyl-3,5,6-trimethylphenol [2.0 g (8.5 mmol)] was added dropwise while stirring, bromine [1.36 g (8.5 mmol)]. To the mixture was then added triethylamine (0.3 ml), which was heated for two hours under reflux. The reaction mixture was cooled, washed with water, dried and then concentrated. The concentrate was crystallized from hexane to obtain 5-acetoxy-2-bromomethyl-4,6,7-trimethyl-2,3-dihydrobenzofuran [2.5 g (yield 93.2%)].

In a manner similar to the above, 5-acetoxy-2-bromomethyl-2,4,6,7-tetramethyl-2,3-dihydrobenzofuran was obtained from 4-acetoxy-3,5,6-trimethyl-2-(2-methyl-2propenyl)phenol.

EXAMPLE 1

To a solution of thiophenol [425 mg (3.8 mmol)] in dimethylformamide (10 ml) was added, under ice-cooling, sodium hydride [167 mg (4.2 mmol, content:60%)]. To the reaction mixture was added, after stirring for 20 minutes, a solution of 5-acetoxy-2-bromomethyl-4,6,7-trimethyl-2,3-dihydrobenzofuran [1.2 g (3.8 mmol)] dimethylformamide (5 ml). The mixture was stirred for further 30 minutes. The reaction mixture was diluted with water, which was subjected to extraction with ethyl acetate. The extract solution was washed with water, dried and concentrated. The concentrate was crystallized from isopropylether-hexane to afford 5-acetoxy-4,6,7-trimethyl-2-phenylthiomethyl-2,3-dihydrobenzofuran (Compound 4) [1.2 g (yield : 91.3%)]. In a manner as above, compounds 2, 6, 8, 10, 12 and 18 were synthesized by employing the corresponding thio compounds (3-mercaptopropionic acid, 1-octanethiol, 2-mercaptopyridine, 4-fluorothiophenol, 2-naphthalene thiol and benzyl mercaptan). Incidentally, when 3-mercaptopropionic acid was employed as the starting compound, 2.2 equivalents of sodium hydride was used.

EXAMPLE 2

To a solution of 5-acetoxy-2-(phenylthiomethyl)-4,6,7-trimethyl-2,3-dihydrobenzofuran [1.2 g (3.5 mmol)] in methanol (8 ml) was added a solution of sodium hydroxide (0.6 g) in water (5 ml). The mixture was heated for one hour under reflux under argon atmosphere. The reaction mixture was, after cooling, diluted with water and, then, neutralized with 2N-HCl and followed by extraction with ethyl acetate. The extract solution was washed with water, and dried, then the solvent was distilled off. The residue was crystallized from isopropyl ether-hexane to obtain 5-hydroxy-2-phenylthiomethyl)-4,6,7-trimethyl-2,3-dihydrobenzofuran (Compound 3) (0.85 g).

In a manner as above, compounds 1, 5, 7, 9, 11, 13, 15 and 17 were synthesized by employing the corresponding 5-acetoxy compounds (Compounds 2, 6, 8, 10, 12, 14, 16 and 18).

EXAMPLE 3

To a solution of 5-acetoxy-2-(phenylthiomethyl)-4,6,7-trimethyl-2,3-dihydrobenzofuran (1.0 g) in methanol (10 ml) was added a 1M aqueous solution of sodium periodate (10 ml), and the mixture was stirred at room temperatures for three hours. The reaction mixture was diluted with water, and the reaction product was extracted with ethyl acetate. The extract solution was washed with water and dried, and then the solvent was distilled off. The residue was crystallized from ethyl acetate - isopropyl ether to obtain desired 5-acetoxy-2-(phenylsulfinylmethyl)-4,6,7-trimethyl-2,3-dihydrobenzofuran (Compound 14) (0.72 g).

EXAMPLE 4

To a solution of 5-acetoxy-2-(phenylthiomethyl)-4,6,7-triethyl-2,3-dihydrobenzofuran (1.0 g) in methanol (10 ml) was added a 2M aqueous solution of periodate (10 ml). The mixture was heated for 14 hours under reflux. The reaction mixture was, after cooling, diluted with water. The reaction product was extracted with ethyl acetate. The extract was washed with water and dried, and then the solvent was distilled off. The residue was crystallized from isopropyl ether-ethyl acetate to obtain 1.0 g of the desired 5-acetoxy-2-(phenylsulfonyl)4,6,7-trimethyl-2,3-dihydrobenzofuran (Compound 16).

The physico-chemical properties of the compounds obtained above are shown in Table 2.

TABLE 2

[Structure: benzofuran with $R^4O$, Me, Me, Me substituents, and $CH_2XR^2$, $R^1$ on the 2-position]

| Compd. No. | $R^1$ | X | $R^2$ | $R^4$ | Yield (%) | m.p. (°C.) | NMR(δppm) CDCl$_3\phi$ |
|---|---|---|---|---|---|---|---|
| 1 | H | S | —(CH$_2$)$_2$CO$_2$H | H | 87.3 | 132–133 | 2.10(9H), 2.50–3.30(8H), 4.85(1H), 5.10(2H); in DMSO-d$_6$ |
| 2 | H | S | —(CH$_2$)$_2$CO$_2$H | Ac | 61.9 | 126–127 | 1.97(6H), 2.07(3H), 2.30(3H), 2.50–3.50(8H), 5.15(1H), 11.00(1H); in DMSO-d$_6$ |
| 3 | H | S | Ph- | H | 81.2 | 108–109 | 2.07(3H), 2.13(6H), 2.80–3.10(4H), 4.17(1H), 4.85(1H), 7.20–7.50(5H) |
| 4 | H | S | Ph- | Ac | 91.3 | 77–78 | 1.97(6H), 2.07(3H), 2.30(3H), 2.80–3.50(4H), 4.90(1H), 7.20–7.50(5H) |
| 5 | H | S | —(CH$_2$)$_7$CH$_3$ | H | 80.4 | 84–85 | 1.20(3H), 1.20–1.70(10H), 2.10(9H), 2.20–3.20(6H), 4.13(1H), 4.83(1H) |
| 6 | H | S | —(CH$_2$)$_7$CH$_3$ | Ac | 73.7 | — | 0.87(3H), 1.10–1.70(10H), 1.97(6H), 2.07(3H), 2.30(3H), 2.30–3.30(6H), 4.90(1H) |
| 7 | H | S | 2-Py- | H | 57.0 | 141–142 | 2.10(9H), 2.90–3.80(4H), 4.17(1H), 5.00(1H), 6.95(1H), 7.20(1H), 7.45(1H), 8.38(1H) |
| 8 | H | S | 2-Py- | Ac | 85.4 | 91–92 | 1.97(6H), 2.07(3H), 2.30(3H), 2.95(1H), 3.27(1H), 3.38(1H), 3.67(1H), 5.05(1H), 6.95(1H), 7.17(1H), 7.45(1H), 8.40(1H) |
| 9 | H | S | 4-F—Ph- | H | 64.8 | 123–124 | 2.03(3H), 2.10(6H), 2.80–3.40(4H), 4.13(1H), 4.83(1H), 6.97(2H), 7.42(2H) |
| 10 | H | S | 4-F—Ph- | Ac | 86.7 | 118–119 | 2.00(9H), 2.30(3H), 2.80–3.40(4H), 4.90(1H), 6.97(2H), 7.42(2H) |
| 11 | H | S | 2-Nap- | H | 75.0 | 114–115 | 2.00(3H), 2.10(6H), 3.00–3.60(4H), 4.15(1H), 4.93(1H), 7.35–7.60(3H), 7.65–7.90(4H) |
| 12 | H | S | 2-Nap- | Ac | 63.8 | 106–107 | 2.00(9H), 2.30(3H), 3.00–3.60(4H), 4.95(1H), 7.35–7.60(3H), 7.65–7.90(4H) |
| 13 | H | SO | Ph- | H | 84.9 | 150–152 | 2.10(9H), 2.70–3.50(4H), 4.50(1H), 4.70–5.40(1H), 7.45–7.80(5H) |
| 14 | H | SO | Ph- | Ac | 68.8 | — | 2.00(9H), 2.70–3.50(4H), 4.80–5.50(1H), 7.40–7.80(5H) |
| 15 | H | SO$_2$ | Ph- | H | 84.9 | 161–162 | 1.77(3H), 2.07(6H), 2.70–3.80(5H), 5.15(1H), 7.45–7.75(3H), 7.90–8.10(2H) |
| 16 | H | SO$_2$ | Ph- | Ac | 91.5 | 154–155 | 1.73(3H), 1.92(3H), 1.95(3H), 2.28(3H), 2.70–3.80(4H), 5.20(1H), 7.40–7.70(3H), 7.90–8.10(2H) |
| 17 | H | S | —CH$_2$Ph | H | 95.3 | 93–94 | 2.13(9H), 2.50–3.30(4H), 3.80(2H), 4.13(1H), 4.83(1H), 7.20–7.40(5H) |
| 18 | H | S | —CH$_2$Ph | Ac | 82.8 | 97–98 | 1.97(6H), 2.08(3H), 2.30(3H), 2.50–3.30(4H), 3.80(2H), 4.87(1H), 7.20–7.40(5H) |
| 19 | Me | S | Ph- | H | 83.8 | 88–89 | 1.53(3H), 2.00(3H), 2.07(3H), 2.10(3H), 2.85(1H), 3.20(1H), 3.23(2H), 4.10(1H), 7.10–7.40(5H) |
| 20 | Me | S | Ph- | Ac | 98.0 | oil | 1.55(3H), 1.95(3H), 1.99(6H), 2.33(3H), 2.90(1H), 3.20(1H), 3.27(2H), 7.10–7.40(5H) |
| 21 | Me | S | 4-F—Ph- | H | 87.2 | 82–83 | 1.50(3H), 1.97(3H), 2.07(3H), 2.10(3H), 2.85(1H), 3.17(2H), 3.20(1H), 4.10(1H), 6.90(2H), 7.32(2H) |
| 22 | Me | S | 4-F—Ph- | Ac | 98.0 | oil | 1.52(3H), 1.95(6H), 1.97(3H), 2.30(2H), 2.87(1H), 3.20(3H), 6.90(2H), 7.32(2H) |
| 23 | Me | O | —CH$_2$Ph | H | 73.3 | 80–81 | 1.47(3H), 2.12(3H), 2.17(3H), 2.20(3H), 4.48(1H), 3.17(1H), 3.52(1H), 3.75(1H), 4.73(2H), 7.30–7.65(5H) |
| 24 | Me | O | —CH$_2$Ph | Ac | 54.0 | 71–72 | 1.47(3H), 2.03(3H), 2.07(3H), 2.13(3H), 2.17(3H), 2.83(1H), 3.10(1H), 4.13(2H), 4.68(2H), 7.25–7.55(5H) |
| 25 | Me | NH | —(CH$_2$)$_2$Ph | H | 82.3 | 74–75 | 1.42(3H), 2.07(6H), 2.13(3H), 2.60– |

TABLE 2-continued

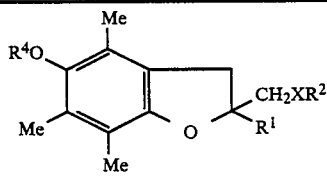

| Compd. No. | R¹ | X | R² | R⁴ | Yield (%) | m.p. (°C.) | NMR(δppm) CDCl₃φ |
|---|---|---|---|---|---|---|---|
| | | | | | | | 3.25(9H), 4.20(1H), 7.23(5H) |

Ph: Phenyl,
Py: Pyridyl,
Ac: Acetyl,
Nap: Naphthyl

| Formulation Example | |
|---|---|
| Capsule | |
| (1) Compound 3 | 50 mg |
| (2) Finely pulverized cellulose | 30 mg |
| (3) Lactose | 37 mg |
| (4) Magnesium stearate | 3 mg |
| Total | 120 mg |

(1), (2), (3) and (4) were mixed, which was filled in a gelatine capsule.

What is claimed is:

1. A compound of the formula:

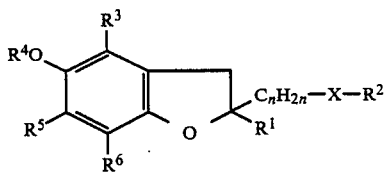

wherein $R^1$ is hydrogen or $C_{1-6}$ alkyl; n is 1; X is sulfide, sulfoxide of sulfone; $R^2$ is $C_{1-10}$ alkyl, $C_{2-10}$ alkenyl, $C_{2-10}$ alkynyl, $C_{3-7}$ cycloalkyl, $C_{3-7}$ cycloalkenyl, phenyl, naphthyl, $C_{1-3}$ alkylphenyl, $C_{1-3}$ alkylinaphthyl, thienyl, pyridyl, imidazolyl, thiazolyl, pyrrolyl, pieridyl, hexamethyleneimidyl, quinolyl, quinuclidyl, indolyl or primidyl, which may be substituted by hydroxy, carboxy, $C_{1-3}$ alkoxycarbonyl, amino, nitro, cyano, halogen $C_{1-3}$ alkoxy, $C_{1-3}$ alkyl, phenyl, $C_{3-6}$ cycloalkyl or pyridyl; $R^3$ is $C_{1-6}$ alkyl; $R^4$ is hydrogen or $C_{1-10}$ alkanoyl; and $R^5$ and $R^6$ each is $C_{1-6}$ alkyl, or a physiologically acceptable salt thereof.

2. The compound according to claim 1 wherein $R^1$ is hydrogen of $C_{1-3}$ alkyl; n is 1; X is sulfinde; $R^2$ is $C_{1-10}$ alkyl which may be substituted by halogen, carboxy or phenyl, phenyl which may be substituted by halogen or $C_{1-3}$ alkoxy, naphthyl or pyridyl; $R^3$ is $C_{1-3}$ alkyl; $R^4$ is hydrogen or acetyl; and $R^5$ and $R^6$ are each $C_{1-3}$ alkyl.

3. The compound according to claim 1, which is 5-hydroxy-2-(phenylthiomethyl)-4,6,7-trimethyl-2,3-dihydrobenzofuran.

4. The compound according to claim 1, which is 5-hydroxy-2-(octylthiomethyl)-4,6,7-trimethyl-2,3-dihydrobenzofuran.

5. The compound according to claim 1, which is 5-hydroxy-2-(4-fluorophenylthiomethyl)-4,6,7-trimethyl-2 3 dihydrobenzofuran.

* * * * *